(12) United States Patent
Majava et al.

(10) Patent No.: US 11,617,527 B2
(45) Date of Patent: Apr. 4, 2023

(54) MUSCLE LOAD MONITORING

(71) Applicant: Polar Electro Oy, Kempele (FI)

(72) Inventors: Ville Majava, Kempele (FI); Pertti Puolakanaho, Kempele (FI); Jonna Puurunen, Kempele (FI)

(73) Assignee: Polar Electro Oy, Kempele (FI)

( * ) Notice: Subject to any disclaimer, the term of this patent is extended or adjusted under 35 U.S.C. 154(b) by 385 days.

(21) Appl. No.: 16/808,759

(22) Filed: Mar. 4, 2020

(65) Prior Publication Data

US 2020/0338393 A1   Oct. 29, 2020

(30) Foreign Application Priority Data

Apr. 23, 2019   (EP) .................... 19170535

(51) Int. Cl.
*A61B 5/22*   (2006.01)
*G16H 20/30*   (2018.01)
*A63B 71/06*   (2006.01)
*A63B 24/00*   (2006.01)

(52) U.S. Cl.
CPC ............ *A61B 5/224* (2013.01); *G16H 20/30* (2018.01); *A63B 71/0622* (2013.01); *A63B 2024/0065* (2013.01); *A63B 2071/0661* (2013.01); *A63B 2220/51* (2013.01); *A63B 2225/50* (2013.01)

(58) Field of Classification Search
CPC .... A61B 5/224; G16H 20/30; A63B 71/0622; A63B 2024/0065; A63B 2071/0661; A63B 2220/51; A63B 2225/50

USPC ............................................. 73/379.01; 482/8
See application file for complete search history.

(56) References Cited

U.S. PATENT DOCUMENTS

| | | | |
|---|---|---|---|
| 9,402,579 B2* | 8/2016 | McLeod | A61B 5/224 |
| 9,737,246 B2* | 8/2017 | Kato | A61B 5/14552 |
| 10,688,345 B1* | 6/2020 | Lynch | G16H 20/30 |
| 2017/0368413 A1* | 12/2017 | Shavit | A61B 5/1123 |
| 2018/0071583 A1* | 3/2018 | Paiz | G16H 40/67 |
| 2019/0111316 A1* | 4/2019 | Su | A61B 5/224 |

OTHER PUBLICATIONS

Extended European Search Report received for European Patent Application Serial No. 19170535 dated Oct. 4, 2019, 2 pages.
Polar, "User Manual Polar Vantage V", URL:https://gzhls.at/blob/ldb/d/l/a/1/1a4e3723f618fbb09f9d15d4a23f682d7cc6.pdf, Oct. 2018, 112 pages.

(Continued)

*Primary Examiner* — Allen Chan
(74) *Attorney, Agent, or Firm* — Fisherbroyles, LLP (57) ABSTRACT

A system for monitoring muscle load, is configured to perform operations including: obtaining, from at least one sensor, measurement data on an exerciser; determining, based on the measurement data, a number of repetitions of a macroscopic movement performed during a physical exercise; determining, based on a conversion entry corresponding to a type of the physical exercise, muscle load coefficient of one or more muscles loaded in the physical exercise; utilizing the muscle load coefficient of the one or more muscles and the number of repetitions in determining muscle load data indicating muscle specific muscle load caused by the physical exercise performed by the exerciser; and outputting the muscle load data.

14 Claims, 8 Drawing Sheets

(56) References Cited

OTHER PUBLICATIONS

Pernek et al., "Exercise Repetition Detection for Resistance Training Based on Smartphones", Personal and Ubiquitous Computing, Springer Verlag, vol. 17, No. 4, Apr. 1, 2013, pp. 771-782.
Chihara et al., "Perceived Discomfort Functions based on Joint Moment for Various Joint Motion Directions of the Upper Limb", Applied Ergonomics, Butterworth Scientific Ltd, vol. 45, No. 2, May 17, 2013, pp. 308-317.

* cited by examiner

|  | 512: MUSCLE 1 | 514: MUSCLE 2 | ... | 516: MUSCLE N |
|---|---|---|---|---|
| 502: FIRST PHYSICAL EXERCISE | X1 | Y1 | ... | N1 |
| 504: SECOND PHYSICAL EXERCISE | X2 | Y2 | ... | N2 |
| ... | | | | |
| 506: N PHYSICAL EXERCISE | XN | YN | ... | NN |

MUSCLE LOAD MONITORING

CROSS-REFERENCE TO RELATED APPLICATION

This application claims benefit and priority to European Application No. 19170535.9, filed Apr. 23, 2019, which is incorporated by reference herein in its entirety.

BACKGROUND

Field

The invention relates to performance monitoring systems. Particularly, the present invention relates to monitoring muscle load of an exerciser.

SUMMARY

Performance of an exerciser is normally measured utilizing measurements like heart rate. Heart rate may be an effective way to monitor, for example, training load of the exerciser, but it may fail to reveal detailed effects of exercise on muscles of the exerciser. Therefore, there is a need to develop solutions that enhance physical exercise performance monitoring, and in particular monitoring of muscle load.

A smart coaching service with an in-built mechanism of transforming type of physical activity or exercise into training load of muscular components, i.e. muscle load is proposed. Different types of physical exercises may be related to different types of overall body motion (can be referred to as macroscopic movements). These different types of body motions may cause different loads to muscular components. The proposed solution may convert types of physical exercises into muscle load by applying a conversion framework.

According to an aspect, there is provided the subject matter of the independent claims. Some embodiments are defined in the dependent claims.

One or more examples of implementations are set forth in more detail in the accompanying drawings and the description below. Other features will be apparent from the description and drawings, and from the claims.

BRIEF DESCRIPTION OF DRAWINGS

In the following embodiments will be described in greater detail with reference to the attached drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
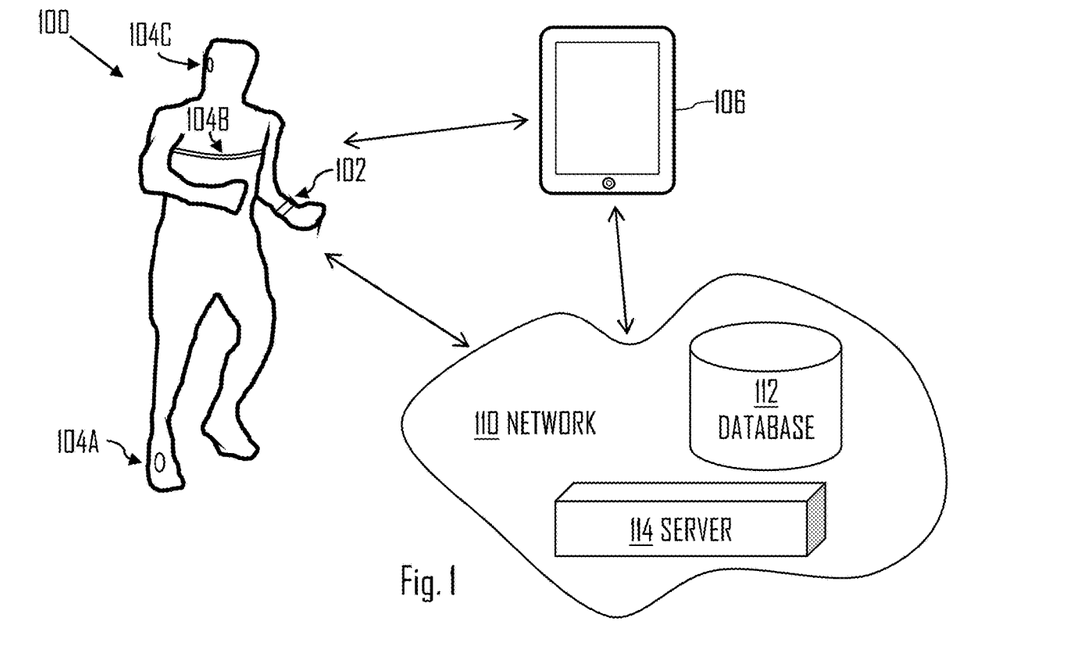
FIG. 1 illustrates an example system to which embodiments may be applied.

FIG. 1 illustrates a system to which embodiments of the invention may be applied. Said system may be used to monitor physical training, activity, and/or inactivity of a user 100. Thus, the embodiments may not be limited to monitoring and/or measuring physical training of the user 100, and thus said system may be used to monitor physical activity and/or inactivity during the day and/or night (e.g. 24 hours a day). Such may be possible using one or more devices described with respect to FIG. 1 and in the embodiments below.

According to an aspect, the system of FIG. 1 a physical exercise monitoring system for monitoring muscle load of an exerciser 100 (can be referred to also as user 100 or simply user).

Referring to FIG. 1, the user 100 may wear a wearable device, such as a wrist device 102, a head sensor unit 104C, a torso sensor 104B, and/or a leg sensor 104A. In another example, the wearable device may be and/or be comprised in glasses. In another example, the wearable device is comprised or configured to be coupled with a garment or garments (or apparel). Examples of such garments may include bra(s), swimming apparel, such as swimming suit or cap, and glove(s). The garment or apparel may be worn by the user. In some embodiments, the wearable device is integrated as a part of the garment or apparel. Due to simplicity reasons, let us now describe the wearable device as being the wrist device 102. However, embodiments described in relation to wrist device 102 may be utilized by other types of wearable devices. I.e. the embodiments are not necessarily limited to wrist device or devices 102.

The wrist device 102 may be, for example, a smart watch, a smart device, sports watch, and/or an activity tracking apparatus (e.g. bracelet, arm band, wrist band, or mobile phone to name a few examples). The wrist device 102 may be used to monitor physical activity of the user 100 by using data from internal sensor(s) comprised in the wrist device 102, data from external sensor device(s) 104A-C, and/or data from external services (e.g. training database 112). It may be possible to receive physical activity related information from a network 110, as the network may comprise, for example, physical activity-related information of the user 100 and/or some other user(s). Thus, the wrist device 102 may be used to monitor physical activity related information of the user 100 and/or the other user(s). It is possible that one or more of the external sensor device(s) 104A-C may be worn by the other user(s), and thus information received from said one or more sensor device(s) 104A-C may be monitored from the wrist device 102 by the user 100 (e.g. a trainer or a coach). The network 110 may comprise the training database 112 and/or the server 114. The server 114 may be configured to enable data transfer between the training database 112 and some external device, such as the wearable device. Hence, the database 112 may be used to store cardiac activity measurement data and/or muscle load data (this is discussed later in more detail), for example.

It needs to be understood that the wrist device 102 may be used to monitor physical activity of the user 100 and/or to be used as a smart watch configured to enable communication with, for example, a portable electronic device 106, the network 110, and/or some other network, such as a cellular network. Thus, for example, the wrist device 102 may be connected (i.e. wirelessly connected) to the portable electronic device 106, such as a mobile phone, smart phone, tablet and/or computer to name a few. This may enable data transfer between the wrist device 102 and the portable electronic device 106. The data transfer may be based on Bluetooth protocol, for example. Other wireless communication methods, such as Wireless Local Area Network (WLAN) and/or Near Field Communication (NFC), may also be used. It is also possible to utilize wired communication methods, such as LAN or Universal Serial Bus (USB), for the data transfer.

In case of communicating directly with the cellular network, the wrist device 102 may comprise similar communication capabilities as mobile devices, such as 2G, 3G, LTE, LTE-A, 4G and/or 5G communication capabilities. Thus, for example, the wrist device 102 may comprise the communication circuitry capable of operating on said technologies, a Subscriber Identification Module (SIM) and/or a memory comprising a virtual SIM configured to provide a secured identification for the wrist device 102 when operating with the cellular network. It is also pointed out that, in general, the wearable device may comprise a communication circuitry capable of cellular, Bluetooth (e.g. BLE), NFC, WLAN, ANT, ANT+, LAN and/or USB communication.

The wrist device 102 may be used to monitor activity and/or inactivity of the user 100. Similarly, or alternatively, the portable electronic device 106 may be used to monitor the activity and/or inactivity of the user 100. Such may require the portable electronic device 106 to acquire physical activity-related data from the wrist device 102, some other wearable device, and/or from external sensor device(s) 104A-C. However, it may be that the portable electronic device 106 determines activity and/or inactivity of the user 100 by utilizing internal sensor(s), such as accelerometer or satellite positioning circuitry.

The wrist device 102 may comprise a cardiac activity circuitry (see e.g. circuitry 214 in FIG. 2) configured to determine cardiac activity of the user 100, such as heart rate, Heart Beat Interval (HBI) and/or Heart Rate Variability (HRV), for example. The cardiac activity circuitry may comprise an optical cardiac activity sensor unit configured to measure the cardiac activity of the user 100. Example of such sensor may be a PPG (photoplethysmography) sensor. Different types of cardiac activity sensors can be used and therefore the type may be some other than the optical cardiac activity sensor. The optical cardiac activity sensor unit may detect the cardiac activity of the user 100 by optical measurement, which may comprise emitting light towards body tissue of the user 100 and measuring the bounced, reflected, scattered and/or emitted light from the body tissue of the user 100. The emitted light may alter when travelling through veins of the user 100 and the alterations may be detected by the optical cardiac activity sensor unit. By using the detected data, the wrist device 102, may determine cardiac activity of the user 100, such as heart rate for example. The optical cardiac activity sensor unit may obtain, via the measurement, a cardiac activity signal characterizing or carrying the cardiac activity information on the user. As understood, similar cardiac activity circuitry may be comprised in some other wearable device additionally or alternatively. For example, armband sensor may utilize optical measurement.

It also needs to be noted that the cardiac activity circuitry may produce raw measurement data of the cardiac activity and/or it may process the measurement data into cardiac activity information, such as heart rate for example. The sensor(s) in the cardiac activity circuitry may comprise data processing capabilities. Also, the wrist device 102 and/or some other device (e.g. portable electronic device 106 and/or server) may comprise a processing circuitry configured to obtain the cardiac activity measurement data from the cardiac activity circuitry (i.e. comprised in the wrist device 102 or some other sensor such as 104B) and to process said data into cardiac activity information, such as a cardiac activity metric characterizing the cardiac activity of the user 100. For example, the measurement data of the optical cardiac activity sensor unit may be used, by the processing circuitry, to determine heart rate, HRV and/or HBI of the user 100. Further, the raw measurement data and/or processed information may be processed by the wrist device 102 or some other wearable device, and/or transmitted to an external device, such as the portable electronic device 106.

The wrist device 102 (or more broadly, the wearable device) may comprise other types of sensor(s). Such sensor(s) may include a Laser Doppler-based blood flow sensor, a magnetic blood flow sensor, an Electromechanical Film (EMFi) pulse sensor, a temperature sensor, a pressure sensor, and/or a polarization blood flow sensor.

In an embodiment, the wearable device comprises a motion circuitry (see e.g. motion circuitry 212 in FIG. 2) configured to measure motion induced by the user 100 to the wearable device, for example, by moving hand (if the wearable device is the wrist device). The motion circuitry or motion sensor(s) discussed herein may comprise one or more gyroscopes, one or more accelerometers, one or more magnetometers and/or one or more barometers. The motion circuitry may use other motion data, such as location data of the user, to determine motion of the user 100. For example, the motion circuitry may comprise a satellite positioning circuitry, such as a global navigation satellite system (GNSS) circuitry. The GNSS circuitry may comprise, for example, a Global Positioning System (GPS) and/or a GLObal NAvigation Satellite System (GLONASS). The satellite positioning circuitry may be used for receiving satellite positioning data. The satellite positioning data may be used, by the wearable device, to determine motion and/or location of the user 100.

In an embodiment, the motion circuitry is a sensor device separate from the wrist device 102.

The motion circuitry may thus comprise one or more sensors worn by the user 100 as separate devices and/or as integrated devices (e.g. integrated to the wrist device 102).

In an embodiment, the motion circuitry comprises at least one of the following: an accelerometer, a magnetometer, and a gyroscope. In an embodiment, the motion circuitry may comprise two or more of said sensors.

In an embodiment, the motion circuitry comprises an accelerometer and a gyroscope. The motion circuitry may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

In an embodiment, the motion circuitry comprises a gyroscope and a magnetometer. The motion circuitry may further comprise sensor fusion software to combine gyroscope data and magnetometer data so as to provide a reference coordinate system for the gyroscope based on the Earth magnetic field measured by the magnetometer. In general, the sensor fusion software described above may combine measurement data acquired from at least two motion sensors such that measurement data acquired from one motion sensor is used to establish the reference coordinate system for the measurement data acquired from at least one other motion sensor. Thus, for example, the satellite positioning data may also be utilized in the sensor fusion.

It is also noted that wrist device 102 is not always necessary to be used. For example, the portable electronic device (PED) 106 may be used to monitor physical performance and/or exercise of the user 100 or plurality of users (e.g. can be used by a trainer of the plurality of users). The PED 106 may be, for example, a mobile phone, smart phone, tablet computer, cycling computer (can be referred to as a bike computer) and/or any other portable device that can be used to receive physical activity data on user or users directly or indirectly from one or more sensors associated with the user or users, and process said data into one or more performance metrics describing, for example, intensity of the physical exercise. Hence, PED 106 and wrist device 102 may be used in a similar way either alone or in combination with each other to monitor physical performance of the user 100 or users.

As already discussed, the user 100 may use/wear a plurality of different sensors 104A-C and/or wrist device 102. For example, (s)he may use a sensor (e.g. chest heart rate monitor 104B utilizing electrode-based measurement) to monitor cardiac activity via electrode-based measurement. The sensors 104A-C may comprise a stride sensor and/or head sensor 104C. For example, the head sensor 104C may be used to measure cardiac activity of the user 100. Therefore, for example, the cardiac activity circuitry discussed herein may be located at one device (e.g. sensor or wrist device 102) or may be comprised in two or more physically separate devices utilizing two or more sensors or one sensor and processing in some other device, for example.

So, in general, the system discussed herein may comprise one or more sensors, such as integrated sensors (i.e. integrated with a device or equipment) and separate sensors (i.e. worn as separate devices by the user). The one or more sensors may be communicatively connected with the device that collects and/or processes data from the one or more sensors. Some specific examples are given below how to, for example, enhance the use of motion circuitry and/or motion sensors in the proposed solution.

One of the aspects discussed herein is the measurement of muscle load of the user 100 or users. It is noted that currents systems do not support measurement of muscle load with an acceptable accuracy. For example, cardiac activity can be used to measure overall training intensity (can also be referred to as exerciser intensity) or training load (can also be referred to as exercise load), but it may be difficult to determine, based on the cardiac activity, how much user's muscles were loaded during the exercise. One choice may be to utilize further sensors to measure muscle load during the exercise. However, this would make the measurement system more complex and considerably more expensive. Furthermore, the number of sensors may become even greater if more than one physical exercise or sport is performed. Therefore, it may be beneficial to provide solutions that enhance monitoring of muscle load of the exerciser 100.

Figure 2:
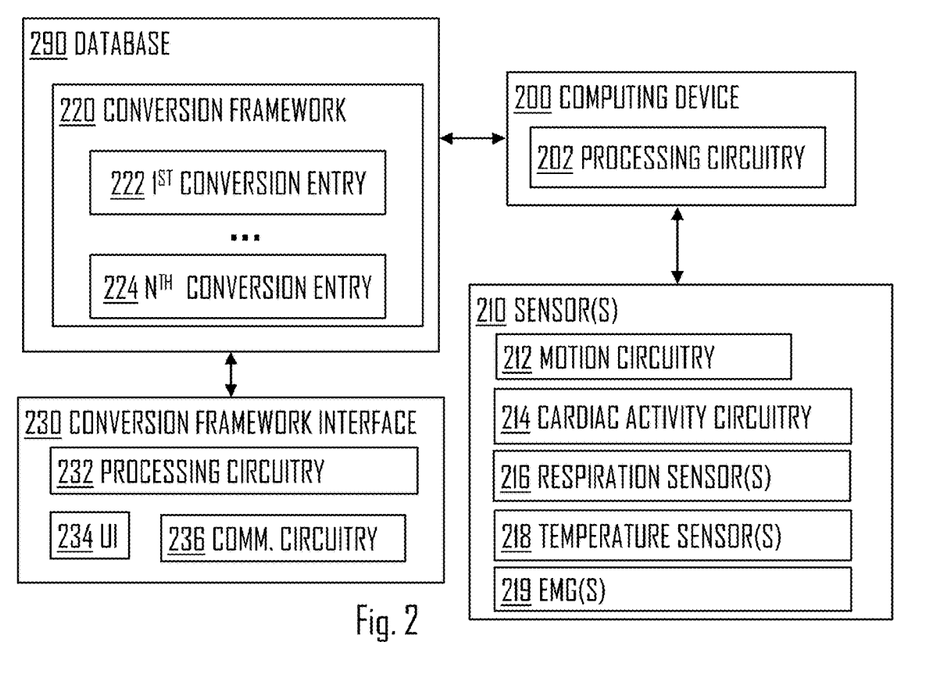
FIG. 2 illustrates a muscle load monitoring system.

FIG. 2 illustrates a system according to some embodiments. The system of FIG. 2 may be a part of the system described in relation to FIG. 1, for example. Therefore, the systems of FIG. 1 and FIG. 2 may share one or more elements with each other, or they may equal to each other.

Figure 3:
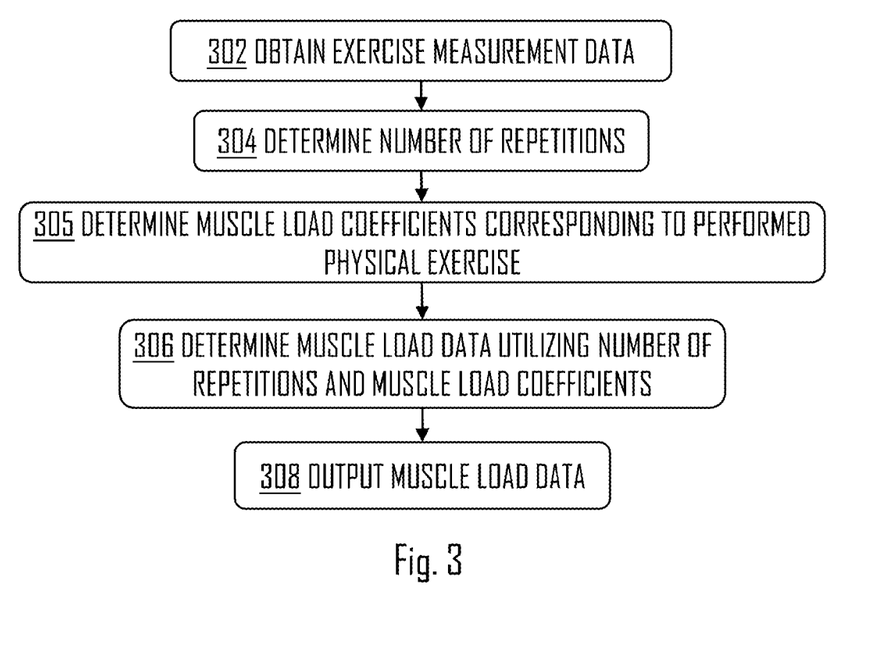
FIG. 3, FIG. 4, FIG. 5, FIG. 6A, FIG. 6B, FIG. 7, FIG. 8, FIG. 9, FIG. 10, FIG. 11, FIG. 12, FIG. 13A, FIG. 13B, FIG. 14A, and FIG. 14B illustrate some embodiments.

The system of FIG. 2 may implement method shown in an embodiment of FIG. 3, wherein the method comprises: obtaining, from at least one sensor, measurement data on the exerciser (block 302); determining, based on the exercise measurement data, a number of repetitions of a macroscopic movement performed during a physical exercise (block 304); determining, based on a conversion entry corresponding to a type of the physical exercise, muscle load coefficient of one or more muscles loaded in the physical exercise (block 305); utilizing the muscle load coefficient of the one or more muscles and the number of repetitions in determining muscle load data indicating muscle specific muscle load caused by the physical exercise performed by the exerciser (block 306); and outputting the muscle load data (block 308).

According to an embodiment, the actions performed in block 304, i.e. determining number of repetitions, may be omitted or determined based on user input, for example. Therefore, the system may implement a method in which the muscle load caused by a physical exercise is determined based on the conversion framework.

According to an embodiment, the measurement data obtained in block 302 is referred to as exercise measurement data. Exercise measurement data is used as an example below but can also be understood generally as measurement data.

The outputting in block 308 may comprise, for example, transmitting the data to an external device (e.g. PED 106 or database 290 or 112). Outputting may additionally or alternatively comprise computing a muscle load indicator based on the muscle load data and outputting the indicator via the computing device's 200 user interface (e.g. via wrist device 102 user interface). Outputting may thus comprise visual, audible and/or haptic output. The muscle load may, in general, be used to monitor muscle load status of the user. One example of this is shown in FIG. 13B which is discussed later.

Prior to block 305, according to an embodiment, the computing device 200 determines the conversion entry from the conversion framework corresponding to the type of the physical exercise.

Referring to FIG. 2, the system may comprise a computing device 200 comprising a processing circuitry 202. For example, the processing circuitry 202 may be configured to cause the computing device 200 to perform the actions of the computing device 200. Such actions are discussed later in more detail, but may comprise, for example, the steps of the method discussed with respect to FIG. 3. The processing circuitry 202 may be implemented, for example, with a specific circuitry or circuitries, or with at least one processor that implements a computer program code stored in at least one memory of the computing device 200. The computing device 200 may be or be comprised in the wrist device 102, for example. However, the computing device 200 may be or be comprised in some other device of the system.

The system may further comprise at least one sensor 210. The at least one sensor may comprise one or more of the sensors described with respect to FIG. 1, for example. Therefore, the at least one sensor 210 may comprise sensors external to the wrist device 102 or sensor(s) that are comprised in the wrist device 102.

According to an embodiment, the at least one sensor 210 comprises the motion circuitry 212, the cardiac activity circuitry 214, a respiration sensor 216, a temperature sensor 218, and/or electromyography (EMG) sensor 219. Each of these sensors may be external to the device 102 or be comprised in the device 102. Sensors external to the device 102 may be integrated with equipment (e.g. skiing pole or weightlifting equipment (e.g. integrated in weights)) or be worn by the user, for example. The system may further comprise a database 290 comprising a conversion framework 220 comprising a plurality of conversion entries 222, 224, wherein each conversion entry 222, 224 is associated with a certain type of physical exercise and indicates a correlation between the certain type of physical exercise and muscle load coefficient of each of a plurality of muscles. The conversion framework is discussed in more detail with reference to FIG. 5. The database 290 may be the database 112 or some other database, for example.

As noted with arrows in FIG. 2, the computing device 200 may be communicatively coupled (e.g. wireless or wired coupling) with the at least one sensor 210 and/or with the database 290 (and thus with the conversion framework 220). For example, the computing device 200 may comprise a communication circuitry enabling the communication with the sensor(s) 210 and/or with the database 290. If the sensor(s) 210 and/or database 290 are comprised in the computing device 200, the communication circuitry may not be needed for such purpose.

In FIG. 2, conversion framework interface 230 is shown which illustrates a further embodiment. The conversion framework interface 230 may be communicatively coupled with the database 290 and configured to enable insertion of a conversion entry into the conversion framework 220 without a need to update the entire conversion framework 220. The inserted conversion entry may be associated with a user selected type of physical exercise, for example. So, the user (e.g. user 100) may insert new conversion entries to the framework 220, update existing conversion entries and/ or delete conversion entries from the framework 220. The conversion framework interface 230 may comprise means to enable the interaction with the database 290. Such means may comprise, for example, a processing circuitry 232, user interface (UI) 234 and/or communication circuitry 236.

In an embodiment, the computing device 200 comprises the conversion framework interface 230.

In an embodiment, the conversion framework interface 230 is separate from the computing device 200.

For example, the conversion framework interface 230 may be implemented at the server 114 and/or PED 106.

Figure 4:
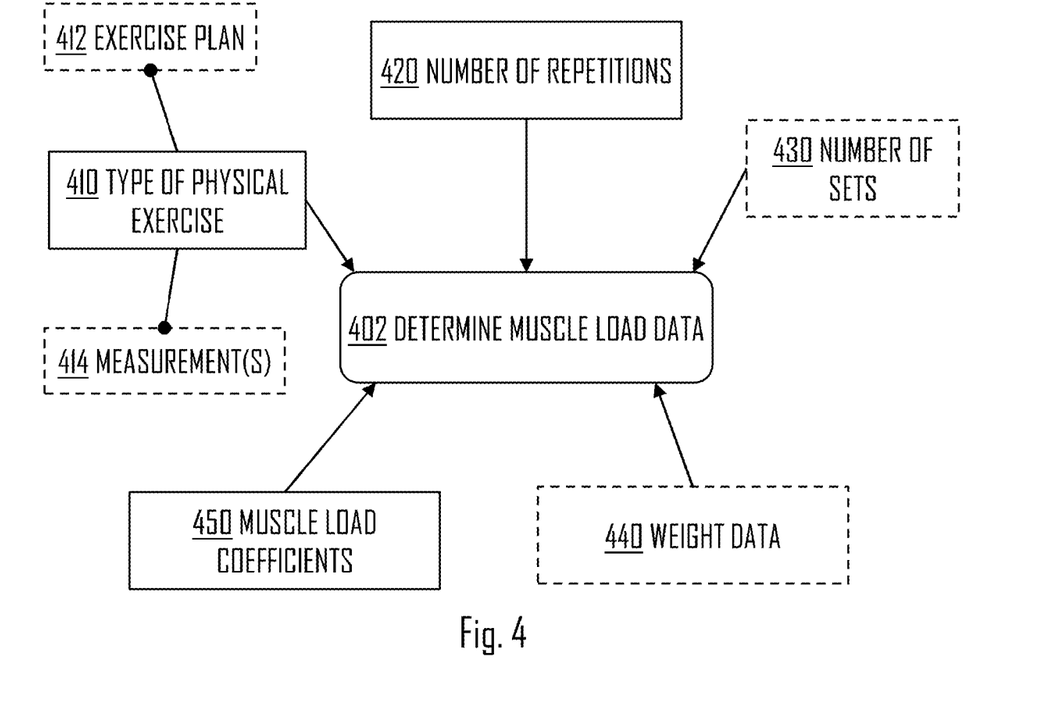

FIG. 4 illustrates an embodiment. Referring to FIG. 4, the computing device may determine muscle load data in block 402. Block may be same or similar as block 306. For example, the muscle load data may be determined based on number of repetitions 420, type of physical exercise 410 and the muscle load coefficients 450. As noted earlier, the muscle load coefficients 450 may be obtained from the conversion framework's 220 conversion entry that is associated with the performed type of physical exercise 410.

According to an embodiment, the computing device 200 is further configured to obtain weight data 440 indicating weight, weights and/or resistance used in a strength training; and utilize the weight data 440 in determining the muscle load data (block 402). For example, the physical exercise performed by the user 100 may be weight training or strength training with weights. Examples of such weighted training may comprise squats, chest-fly, and/or bench-press. It is also noted that the strength training may refer to body weight exercises. Hence, in such situations the weight data 440 may indicate, for example, body weight of the user 100. If additional weights are used in the body weight exercise, the weight data may indicate the additional weight and the body weight of the user 100. For example, pull-ups may be performed using an additional weight. One example of resistance used in the strength training may relate to used resistance with gym equipment, such as pneumatic resistance or resistance produced with a motor (e.g. electric motor). In broader concept, weight or weights can be understood also as resistance used in the training. Therefore, resistance may cover strength training with free weights and with certain equipment configured to produce selected/ indicated resistance. So, weight data may indicate, for example, used free weights, user's weight and/or resistance associated with a certain equipment.

In an embodiment, the computing device 200 determines, based on the exercise measurement data, number of sets 430 of the macroscopic movement and utilizes the number of sets in determining the muscle load data (block 402). The computing device 200 may determine the number of repetitions in each of the number of sets. For example, strength training may be performed in sets, e.g. three sets, ten repetitions in each set equaling to 30 repetitions in total. Different set structures can be utilized (e.g. 2×6, 3×8-12 to name a few examples). It may be beneficial to determine the number of sets in addition to the number of repetitions as, for example, 30 repetitions in a row may cause different muscle load than performing the 30 repetitions in three sets. Taking into account the number of sets, this difference may be taken into account in determining the muscle load data.

The type of the physical exercise 410 performed by the user may be determined based on the exercise measurement data 414 and/or based on a physical exercise plan 412. For example, the physical exercise plan may indicate that the user needs to perform certain exercise today, and thus the determination of the type of physical exercise 410 may be based solely on the exercise plan 412. On the other hand, the computing device 200 may determine e.g. a certain motion pattern from the exercise measurement data that corresponds to a certain predefined motion pattern. Said predefined motion pattern may on the other hand be associated with a certain type of physical exercise, and thus the type of performed physical exercise may be determined. It is also possible that the computing device 200 utilizes both data sources (i.e. 412, 414) in determining the type of the performed physical exercise 410. It is also simply possible that the user inputs or selects the type of physical exercise 410 which (s)he is performing.

The exercise plan 412, if such is available, may include for example type of physical exercise and duration, and target intensity (for example in terms of heart rate or power). Alternatively, for example, exercise plan may include a planned gym routine with types of physical exercise (corresponding to types of overall body motions) and number of repetitions and/or weights applied. Therefore, the number of repetitions may be obtained from the exercise plan instead or in addition to the determining the repetitions based on exercise measurement data.

In an embodiment, the number of repetitions is obtained from the exercise plan 412, wherein the computing device 200 validates and/or verifies the number of repetitions based on the exercise measurement data. For example, the exercise plan may indicate that 10 repetitions are needed. The computing device 200 may determine whether or not the user performs the needed 10 repetitions.

Figure 8:
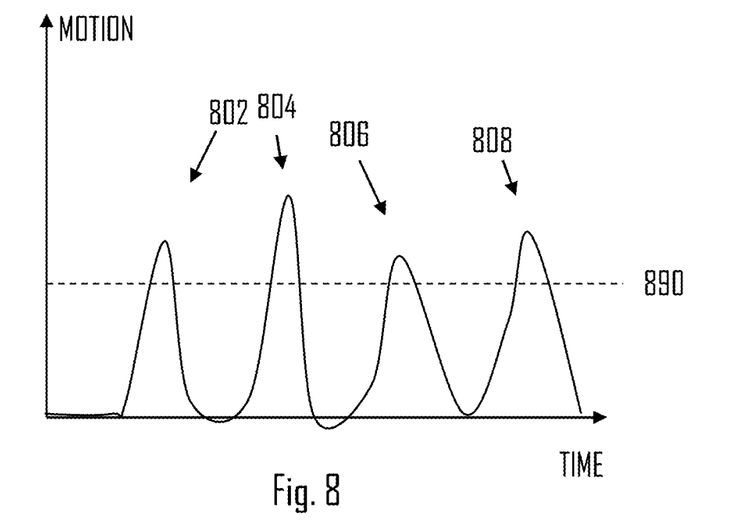
Figure 9:
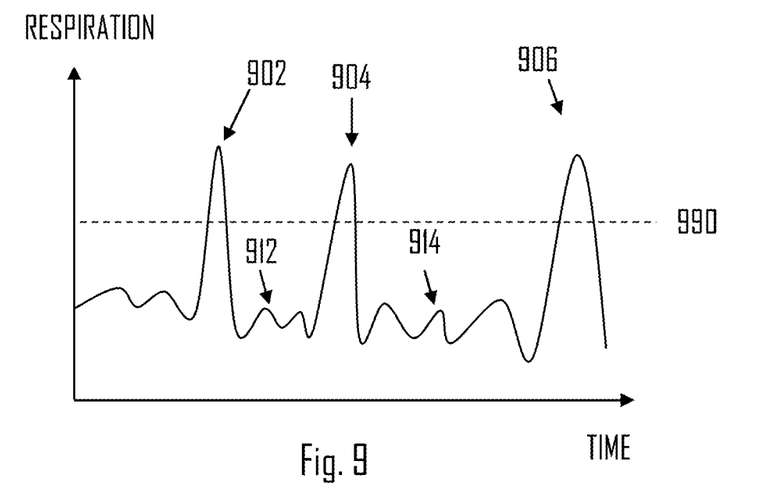
Figure 10:
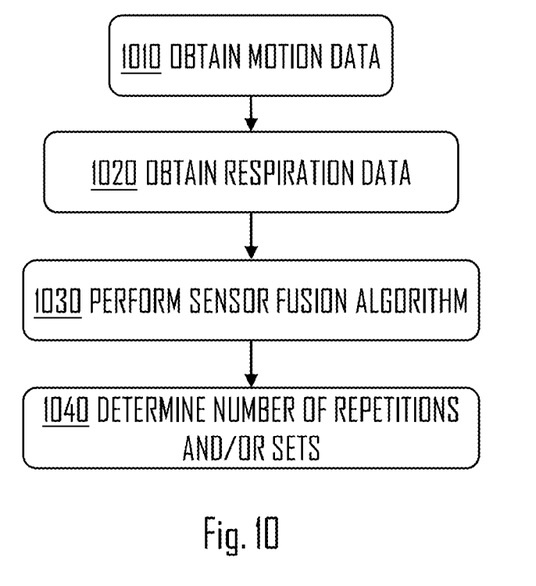

FIG. 8, FIG. 9, and FIG. 10 illustrate some embodiments which relate to the determining of the type of physical exercise and/or determining the number of repetitions and/or sets. As noted above, in an embodiment, the number of repetitions 420 is determined based on the exercise measurement data provided by the at least one sensor 210.

According to an embodiment, the exercise measurement data comprises motion data, wherein the determining the number of repetitions is based on the motion data. The motion data may be obtained using, for example, the motion circuitry 212. Referring to FIG. 8, one example of determining repetitions 802-808 based on the motion data may be seen. The repetitions may be observed, for example, from motion exceeding a threshold 890. The motion may refer to, for example, acceleration or speed. It is possible that more than one motion sensor, such as inertial sensor, is used in determining the number of repetitions. For example, one motion sensor can be located at wrist of the user (e.g. in wrist device 102) and one at a chest of the user (e.g. external chest sensor). Utilizing more than one sensor may enable determining the number of repetitions of different type of physical activity. For example, during pull-ups or push-ups, wrist of the user may be immobile, and hence the chest sensor (or some other placement) may be beneficial. It is also possible that chest of the user is immobile (e.g. bench press or push press) and thus the wrist sensor may be beneficial.

Therefore, in an embodiment, the number of repetitions and/or sets is determined based on exercise measurement data (e.g. motion data) obtained using two or more sensors (e.g. motions sensors, such as inertia sensors). The two or more sensors may be configured to be placed (e.g. attached) at different locations at/on the user's body. For example, one sensor can be located at first location (e.g. wrist) and the other at a second location (e.g. chest). Using several sensors may enable the macroscopic movement to be recognized and analyzed with enhanced accuracy. The different sensors may further be configured to communicate with each other via sensor interface, thus enabling further accuracy in determining the repetitions. The sensor interface may be located at the computing device 200, for example.

According to an embodiment, the exercise measurement data comprises respiration data, wherein the determining the number of repetitions is based on the respiration data. The respiration data may be obtained using, for example, the respiration sensor 216. For example, in strength training, the user usually synchronizes his respiratory on repetitions of macroscopic movements. When respiration is measured during movement, it can give direct measurement or enhancement for repetition counter. Respiration can be measured by any technique available such as dynamic heart rate (e.g. measured with electrode-based chest sensor), movement measurement by accelerometer (e.g. measured with motion sensor placed at the chest) and/or strain measurement (e.g. measured with strain sensor). Example of determining repetitions based on respiration data may be seen in FIG. 9 in which repetitions 902-906 may be observed similarly as from the motion data. It is noted that there can be other inhale/exhale patterns 912, 914 in the respiration data which may not correspond to the repetitions. Hence, for example, the repetitions 902-906 may be calculated at locations where respiration exceeds a threshold 990 (e.g. deep inhale and/or exhale).

In an embodiment, with reference to FIG. 10, the computing device 200 obtains motion data (block 1010) and respiration data (block 1020), and performs (block 1030) a sensor fusion algorithm to determine (block 1040) the number of repetitions, wherein the sensor fusion algorithm utilizes the motion data and the respiration data. The sensor fusion algorithm may be performed, e.g. at the sensor interface of the computing device 200. This approach may further enhance the calculation of the repetitions as measurements from different sensors and/or different metrics may enhance the accuracy and/or robustness of the calculation.

In addition to determining the number of repetitions and/or sets, the different sensors 210, user input and/or exercise plan 412 may be used to determine the performed physical exercise or exercises.

According to an embodiment, the computing device 200 obtains motion data from at least one motion sensor integrated with equipment, such as weights. For example, weightlifting bar or some other equipment utilized by the user may comprise an integrated motion sensor which measures the motion of the bar. From the motion data, the computing device may determine the number of repetitions.

In an embodiment, the weight data (see block 440) is determined based at least partially based on information received from an integrated sensor. For example, at least one weight (or each weight) may comprise an integrated sensor. Therefore, the integrated sensor may be associated with a certain weight. This association may be predetermined by the computing device 200 (i.e. the computing device 200 may determine the weight data based on the identifier of the integrated sensor) or indicated by the sensor data transmitted from the integrated sensor to the computing device 200. The integrated sensor may be, for example, a motion sensor providing motion data or simply a tag that indicates the weight(s).

Figure 5:
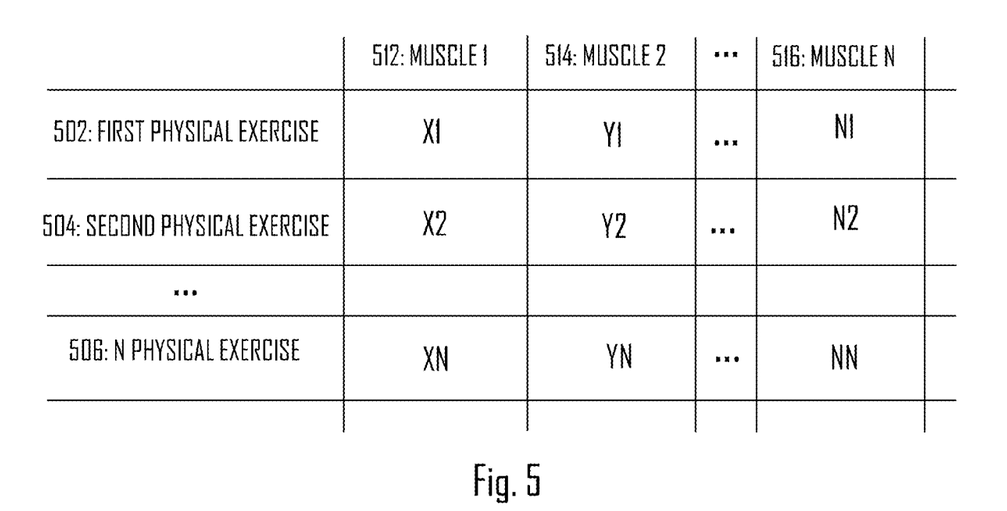

Let us then draw our attention to the conversion framework 220. FIG. 5 illustrates the conversion framework 220 according to an embodiment. Referring to FIG. 5, physical exercises 502, 504, 506 are listed on the rows and muscles 512, 514, 516 on the columns. Therefore, the conversion framework can be understood as a table or a matrix.

Physical exercises 502, 504, 506 may comprise, but are not necessarily limited to, running, skiing, rowing, swimming, and/or strength training, such as ab crunch, bicycle crunch, alternate finger to toes crunch, sit-up, plank, side plank with a crunch, scorpion, march and reach, in an out frog crunch, tornado, hip roll, downward dog, side stretch, bench press, chesty fly, push-up, Spiderman push-up, renegade, sphinx, back extension, alternating back extension, Superman, swimming Superman, bent-over row, bent-over dumbbell row, deadlift, sumo deadlift, good morning, seated row, upright row, shoulder press, biceps curl, overhead triceps extension, bench dip, chair dip, and/or lunge. For example, each of the physical exercises 502-506 may correspond to a certain sport or certain strength training exercise. Hence, the macroscopic movement may refer to the performed exercise or to a certain movement that is associated with the physical exercise (e.g. the macroscopic movement is part of the physical exercise). For example, macroscopic movement of bench press may refer to the motion cycle that is performed during the bench press and constitutes one repetition. I.e. one motion cycle may be calculated as one repetition, for example. It is also noted that one physical exercise may be associated with one or more macroscopic movements, and the muscle load caused by each of the one or more macroscopic movements may be determined by the computing device 200.

The muscles 512, 514, 516 may comprise any muscles or muscle groups of the user, particularly a human being. The muscles 512, 514, 516 may comprise calves, quadriceps, hamstrings, glutes, hips, lower back, lats (i.e. Latissimus dorsi), abdominals, pectorals, deltoids, triceps, biceps, and/or forearms.

In an embodiment, the conversion framework additionally or alternatively comprises data element for brain. That is, similarly as for muscles, the different physical exercise may be associated with the brain, and thus the physical exercises may have a coefficient for brain load. Brain health index is discussed later in more detail. In a way, the brain can be understood as a muscle in the sense of the present solution, although brain is physiologically not a muscle but a tissue-based organ.

As said, there may be an association between the different physical exercises and muscles in the form of coefficients, and particularly in the form of muscle load coefficients X1, X2, XN, Y1, Y2, YN, N1, N2, and NN as shown in FIG. 5.

For example, X1 may be muscle load coefficient of muscle 512 caused by the physical exercise 502. Similarly, regarding the physical exercise 502, muscle load coefficients Y1 and N1 are shown for muscles 514 and 516 respectively.

In general, if a physical exercise causes load to a muscle, the muscle load coefficient may indicate a non-zero value (e.g. positive real value). If the physical exercise does not cause load to a muscle (or the muscle load is minimal), the muscle load coefficient may be zero (or substantially zero value). So, for example, if the physical exercise 504 causes muscle load to muscle 514, Y2 may be a non-zero value. For example, if physical exercise 506 does not cause muscle load to muscle 516, NN may be zero. In this way, for each physical exercise, muscle load coefficients may be indicated and/or obtained from the conversion framework. One conversion entry may thus be understood as indicating physical exercise and muscle load coefficients associated with the physical exercise. For example, one conversion entry may comprise the physical exercise 506 and muscle load coefficients XN, YN . . . NN.

The elements of the conversion matrix may be obtained through measurements and/or they may be predetermined based on literature and/or user input. So, for example, the muscle load coefficients may be static, or dynamic in the sense that they may be modified or updated based on measurements, user input and/or software updates.

Figure 6A:
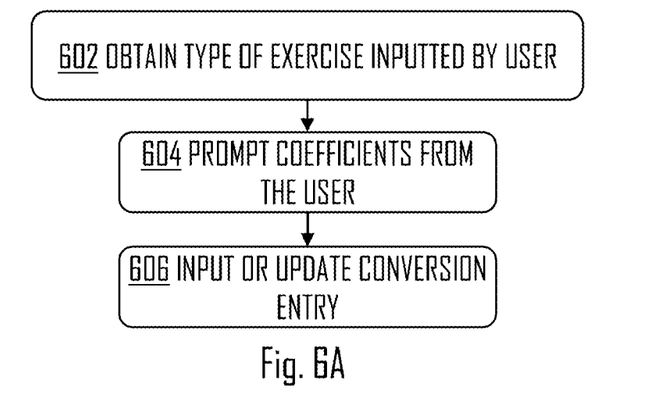

FIG. 6A and FIG. 6B illustrate some embodiments. Referring to FIG. 6A, in block 602, type of physical exercise inputted by a user is obtained, for example, by the conversion framework interface 230 via UI 234. The interface 230 may further prompt the user to input muscle load coefficients associated with the type of physical exercise in block 604. Based on the inputs in block 602, 604, an existing muscles load coefficients of the type of physical exercise may be updated in the conversion framework, or a new conversion entry inputted into the conversion framework. So, let's assume that user inputs bench press (block 602) and the conversion framework already has a conversion entry for bench press. Therefore, in block 604 the user may update/change the muscle load coefficients associated with the bench press, and in block 606 these updates may be installed into the conversion framework (e.g. via wireless and/or wired communication interface). In another example, the user inputs a custom physical exercise (e.g. a physical exercise that (s)he has invented her-/himself). Therefore, in block 604, muscle load coefficients of this custom physical exercise may be prompted, and once inputted the custom physical exercise and its muscle load coefficients may be inputted into the conversion framework in block 606. It is noted that the new physical exercise does not necessarily have to a custom physical exercise. However, the use of the proposed conversion framework enables the user to input her/his favorite exercises into the system, and efficiently monitor muscle load caused by these exercises.

Figure 6B:
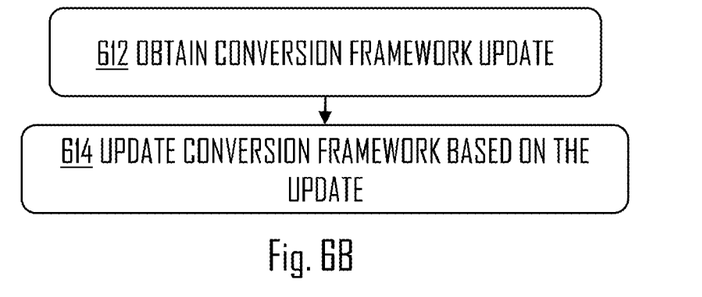

Referring to FIG. 6B, in block 612 the conversion framework interface 230 obtains a conversion framework update. Said update may be, for example, a new conversion entry, muscle load coefficient update (e.g. adjustment of muscle load coefficient values or providing new coefficients) or a deletion of a conversion entry. It is noted that the used conversion framework may enable updates to the data structure without the need to change the data structure. E.g. a new custom conversion entry may be inserted without a need to update the whole data structure. This approach may enable the updates to be incremental (i.e. only the update is transferred via communication interface), and therefore there may be no need to update the whole conversion framework and the logic behind the conversion framework. So, the logic enabling the use of the conversion framework may be implemented with static software code/program as there may be no need to update the logic because the logic may remain the same even if new conversion entries are inserted. Therefore, in block 614, based on the update obtained in block 612, the conversion framework may be updated.

Figure 7:
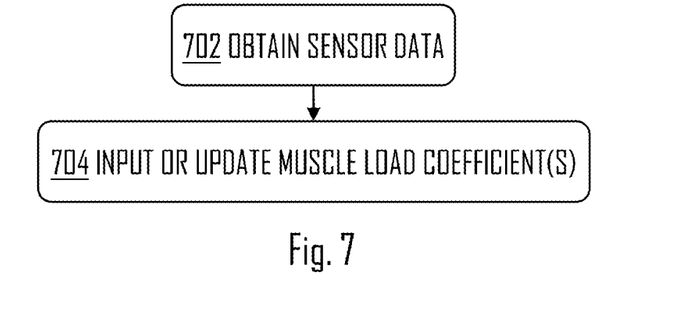

FIG. 7 illustrates an embodiment relating to measuring muscle load coefficients. Referring to FIG. 7, in block 702, the conversion framework interface 230 may obtain sensor data, and in block 704 input or update muscle load coefficient(s) based on the sensor data. For example, the system may comprise one or more EMG sensor (e.g. see 219 in FIG. 2), wherein, for at least one type of physical exercise, muscle load coefficients may be obtained and/or updated based on performing one or more electromyography measurements utilizing the one or more EMG sensor. Instead or in addition to using EMG sensor for updating and/or obtaining the muscle load coefficients, muscle oxygen sensor may be utilized. It is understood by the skilled person that the measurement (e.g. EMG measurement) should be done on the muscle or muscles whose muscle load coefficient needs to be determined or updated. The measurement may be done during performing the physical exercise.

In an embodiment, the muscle load coefficients are obtained and/or updated (block 704) in real time based on the sensor data (block 702). Therefore, the coefficients may be updated during performing the physical exercise.

In an embodiment, the system utilizes a calibration or training mode in which the muscle load coefficients are obtained and/or updated based on sensor data. For example, the muscle load coefficients may initially be predetermined, e.g. system standard values. So, the system may use these standard values in determining the muscle load data. However, the calibration or training mode may be used to determine user specific muscle load coefficients based on the sensor data. Therefore, the system standard values stored in the conversion framework may be, for example, updated based on the determined user specific muscle load coefficients. This enables the conversion framework to be user specific. During the training or calibration mode, the user may be instructed to perform the physical exercise whose muscle load coefficients need to be determined and/or updated.

Let us then look at couple of examples what kind of muscle load coefficients can be used. As described above, muscle load coefficient may indicate a coefficient (or percentage) of how much strain or load is caused by a certain physical exercise to a muscle. For example, doing squats may cause muscle load to back, abdomen, and leg muscles: Squat—hamstrings 0.2 (or 20%), buttocks 0.5 (or 50%), thighs 0.2 (or 20%), and back 0.1 (or 10%). For example, for bench-press the muscle load coefficients could be as follows: triceps 0.3 (30%), biceps 0.1 (10%), shoulders 0.3 (30%), and pectoral 0.3 (30%).

Once coefficients of the physical exercise are known or determined, then intensity and volume for squat can be calculated by used weight, repetitions and sets. Let's say general training intensity is about 70% of Repetition Maximum (RM) with 5 repetitions in 5 sets. RM may indicate a maximum weight for a certain number of repetitions. For example, if user can do five repetitions with 100 kilograms, 70% of RM with five repetitions would then be 70 kg. Then muscle load caused by the exercise may be calculated as follows: 20%×70%×5×5=35000 for hamstrings, 50%× 70%×5×5=87500, 20%×70%×5×5=35000 for thighs and 10%×70%×5×5=17500 for back. It may be possible to neglect general intensity and number of sets in the calculation. In this way it would be assumed that general intensity is 100% and number of repetitions comprise reps in all sets.

In an embodiment, each muscle or muscle group is associated with a muscle or muscle group specific factor. The factor may be understood as a corrective factor based on knowledge or muscle tolerance. For example, 10 repetitions in 3 sets may be more strenuous for a first muscle than for a second muscle. One example difference may be observed between large and small muscles, wherein small muscles may recover slower, and therefore the corrective factor may be used. For example, the smaller the muscle is, the greater the corrective factor may be. So, in other words, the larger the muscle is, the smaller the corrective factor may be, for example. It is also noted that, the greater 1RM (i.e. maximum weight that the user can lift once) is, the more the user's muscles involved in the movement (e.g. squat) may tolerate exercise without loosing power. On the other hand, corrective factor may be used to highlight differences between sets. For example, one repetition with maximum effort (e.g. as much as the user can lift, i.e. maximum weights) may be more strenuous than, for example, 10 repetitions in 3 sets with 60% of maximum effort (i.e. maximum weight). Therefore, in an embodiment, the corrective factor is based on weight data. Particularly, the corrective factor may be based on ratio of lifted weight or weights and maximum weight the user can lift. So, for example, if the user can bench press 100 kilograms (kg) once, and is performing bench press with 60 kg weights, the ratio may be, for example, 0.6. As noted above, the number of sets and repetitions in each set may also affect the corrective factor, and thus it can be something else than exactly the ratio value (e.g. 0.6 in this example).

In broader context different types of physical exercises, such as different sports or strength training exercises, may have an effect on different types of muscles. For example, whereas running may mostly affect leg muscles, rowing and skiing may have an effect on upper body muscles as well. As for strength training exercise, similar figures can be calculated for each exercise. For example: Running: Core/abdomen 20%, Legs 70%, Buttocks 10%; Skiing: Arms 20%, Back 20%, Abdomen 20%, Buttocks 20%, Legs 40%; and Rowing: Arms 20%, Back 20%, Abdomen 20%, Buttocks 20%, Legs 40%.

As noted above, some of the muscle load coefficients (i.e. indicated either as a value from 0 to 1 or as a percentage, or both) relate to muscles groups and some to specific muscles. For example, if a coefficient is indicated for a muscle group, it may be relevant to all muscles in that muscle group. However, using muscle specific coefficients may provide even more accurate results. In general, muscle load coefficient may be 100%, but often is less than 100% as most physical exercises may not comprise or be isolative movements. For example, if there is a movement or physical exercise that targets only biceps, then the muscle load coefficient may be 100% (or 1) for biceps. Hence, the 100% may be shared between different muscles involved in the movement or physical exercise. Therefore, in an embodiment, sum of muscle load coefficients for a certain physical exercise may be 100% (or 1).

Figure 11:
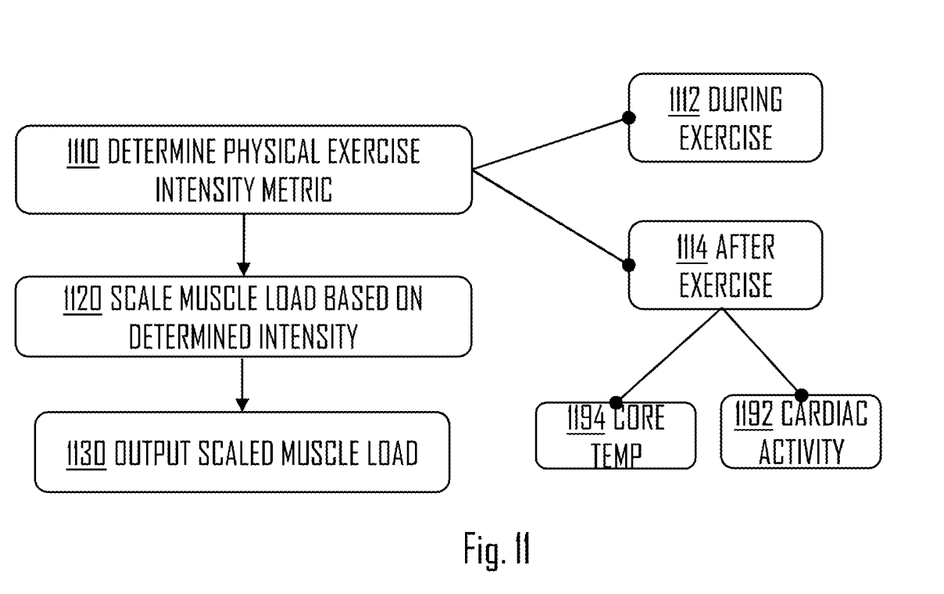

FIG. 11 illustrates an embodiment. Referring to FIG. 11, the computing device 200 may determine, based on the exercise measurement data, a physical exercise intensity metric describing overall intensity of the physical exercise (block 1110); and utilize the physical exercise intensity metric in determining the muscle load data by scaling the muscle specific muscle load based on the physical exercise intensity metric (block 1120). The scaled muscle load data may further be outputted (block 1130).

The intensity metric may be determined based on measurement data on the user obtained during exercise (block 1112) and/or after the exercise (block 1114). The measurement data of blocks 1112, 1114 may comprise, for example, cardiac activity data 1192, such as heart rate, power data, motion data and/or core temperature data 1194. For example, overall intensity of the exercise may be determined from motion circuitry data and/or cardiac activity circuitry data. Based on one or more parameters and/or data, the physical exercise intensity metric may be determined. The duration of measurement after the exercise has ended (i.e. block 1114) may be configurable by the system or may be predetermined (e.g. 1 minute, 10 minutes, 0.5 hours, or 1 hour, to name a few examples).

According to an embodiment, the system is configured to measure, after the physical exercise, at least one of heart rate, core temperature of the user; and utilize at least one of the heart rate, the core temperature in determining the physical exercise intensity metric. This way, the system may estimate so called after burn of the physical exercise. So, the physical exercise metric may indicate at least the after burn of the exercise in this embodiment. The physical exercise metric may thus be called as afterburn index. The afterburn index may be similar to excess post-exercise oxygen consumption (EPOC) measurement or metric. It is noted that one or both of blocks 1112, 1114 may affect the calculation of the exercise intensity metric.

According to an embodiment, the exercise intensity metric equals to training load. So, the exercise intensity metric may be computed based on measured intensity and duration of the exercise (e.g. training load=intensity×duration).

For example, the exercise intensity metric may be used to scale the muscle load of each of the muscles. For example, the scaling may be based on a predetermined standard exercise intensity (e.g. user specific standard exercise intensity) and its relation to the measured exercise intensity. For example, a standard exercise intensity may be associated with a certain heart rate zone or zones. So, when the user is training at an intensity corresponding to the standard exercise intensity, the scaling factor may be 1. If the measured intensity is higher, the factor may increase (i.e. over 1), and if the intensity is lower, the factor may decrease (i.e. below 1). For example, standard exercise intensity could be a certain intensity or heart rate zone, such as 55% to 70% from user's maximum heart rate. So, if average heart rate is over 70%, the muscle load may be scaled upwards with the scaling factor in this example. It is noted that this is just one example of how to use the scaling ability, and therefore there are numerous different examples of how to use the scaling so that the muscle load monitoring is enhanced. In another example, the exercise intensity metric may be compared with exercise intensity metrics of one or more previous exercises (e.g. moving average), and the scaling may be performed based on said comparison. Therefore, the standard exercise intensity may be adapted based on user performance, for example.

Figure 12:
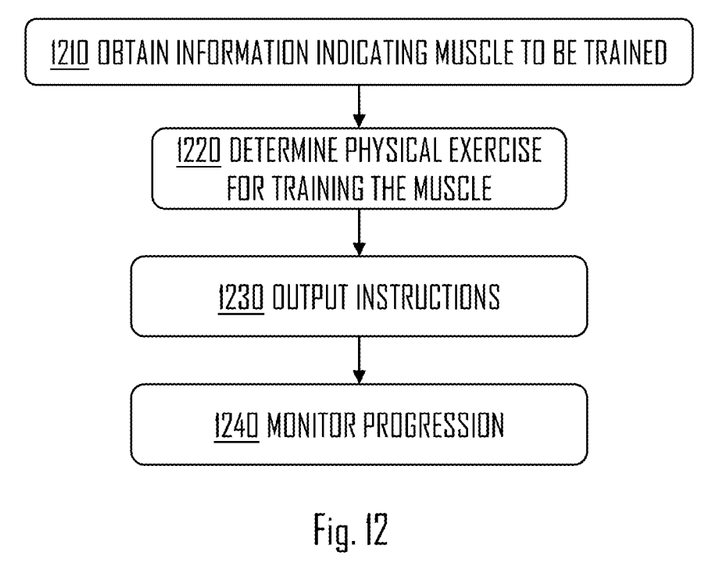

FIG. 12 illustrates an aspect of the proposed solution. Referring to FIG. 12, the system of FIG. 2 (e.g. computing device 200) may be configured to perform the following steps: obtaining information indicating at least one muscle that needs to be trained (block 1210); determining, based on the conversion framework 220 and the obtained information, one or more physical exercises for training the at least one muscle (block 1220); outputting instructions for performing the determined one or more physical exercises (block 1230); and monitoring progression of the at least one muscle via monitoring muscle load of the at least one muscle (block 1240). Basically, the solution described with respect to FIG. 12 may be independent or performed in addition to the above described solution(s). The conversion framework 220 may thus alternatively or additionally used other way around so that the user may obtain training instructions which target improving a certain muscle or muscle group. For example, target may be user defined or system determined. For example, if one or more of user's muscles are determined to be undertrained, the instructions may comprise physical exercises that target the undertrained muscles.

Let us then go through one example of how the muscle load calculation may be implemented. We denote conversion framework as conversion matrix C, utilize an accumulation vector or matrix A, exercise vector or matrix E and further scaling factor c. Based on these elements, the muscle load matrix or vector M may be computed as:

$$M = cCAE.$$

Conversion matrix C and its details were discussed above (see e.g. FIG. 5). The matrix C may be one way to implement the conversion framework.

Accumulation vector or matrix A may indicate the number of repetitions. Further, A may indicate number of sets, number of repetitions in each set, duration of the physical exercise, intensity of the physical exercise, and/or weight data (see 440 in FIG. 4). In some embodiments, the number of repetitions may not be needed and instead the duration and/or intensity (e.g. power or heart rate) may be used to determine the muscle load. For example, skiing for a certain time period with certain intensity may cause certain muscle load to certain muscles. Therefore, repetitions may not necessarily have to calculated.

Exercise vector or matrix E may indicate physical exercises or macroscopic movements of the physical exercises. For example, E may indicate five different physical exercises, or indicate five different macroscopic movements that are performed when performing a certain physical exercise. This way the system may determine what macroscopic movements are performed, and use this information in determining, based on the conversion matrix, the muscle load coefficients related to that specific physical exercise and/or macroscopic movement. Such vector or matrix may be useful as one physical exercise may be associated with one or more macroscopic movements.

Finally, c may be essentially the same as the scaling factor discussed above (i.e. scaling based on overall exercise intensity, see FIG. 11).

M may thus indicate for a muscle or muscles the muscle load caused by the physical exercise. M may additionally or alternatively be an accumulation matrix indicating the accumulated physical load. Regarding the accumulation, it is also noted that the muscle load of muscles may decrease in rest (e.g. decrease with a certain rate which may be muscle specific).

In another example, when utilizing the conversion framework or matrix to obtain training instructions, the training instructions may indicate at least the physical exercises or macroscopic movements of the physical exercises. Effectively, according to an example, instructions may be obtained by solving E from the following equation:

$$E = (1/c)A^{-1}C^{-1}M$$

Thus, at least the instructions outputted to the user may indicate which exercises or macroscopic movements (s)he should perform. Additionally, the number of repetitions (or some other quantity or quantities, e.g. matrix A) may be indicated, but may not be always necessary as the system may compute the number of repetitions as was previously discussed. The instructions may thus be simple instructions or comprise a full training plan for the user.

Figure 13A:
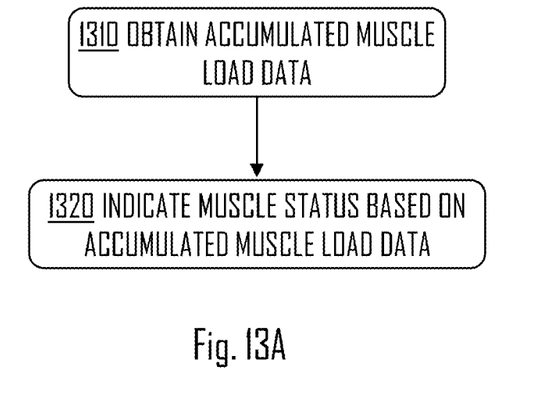
Figure 13B:
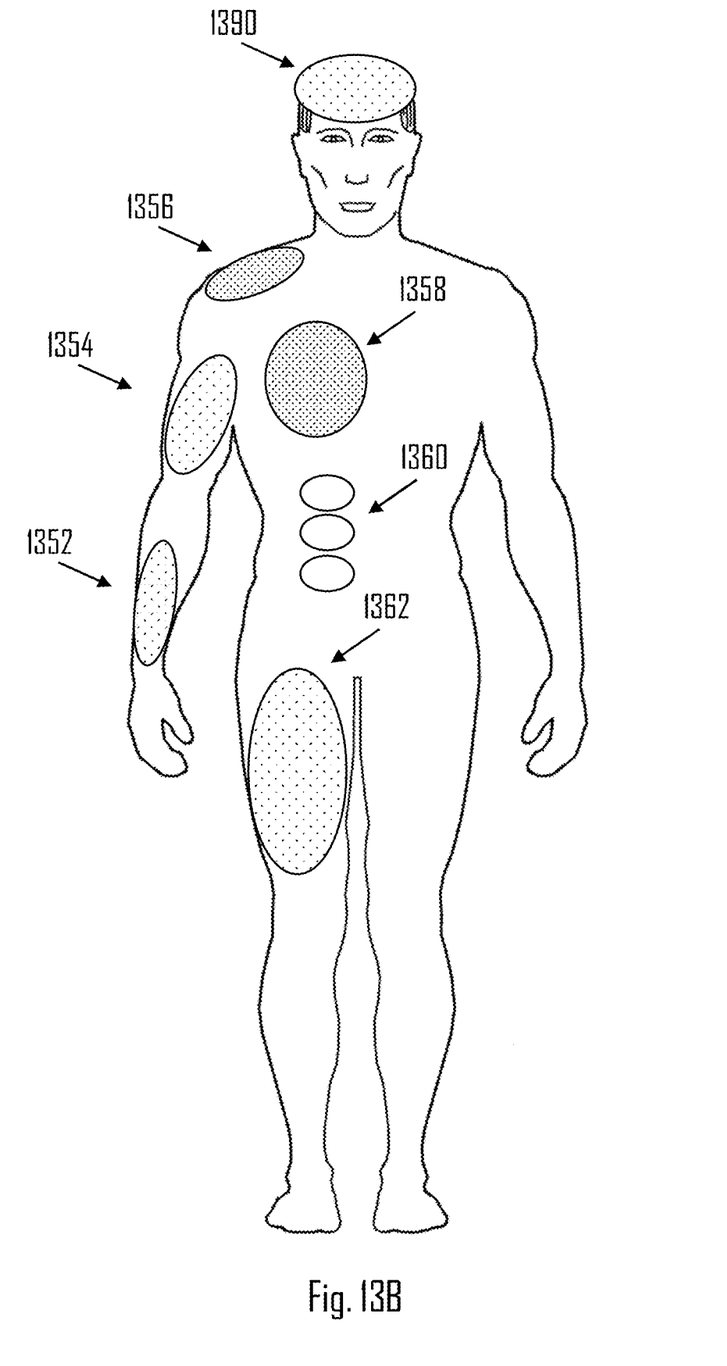

FIG. 13A and FIG. 13B illustrate an embodiment related to the obtaining and indication of accumulated muscle load data. Referring to FIG. 13A, the computing device 200 may obtain accumulated muscle load data by determining muscle load caused by a plurality of different exercise sessions (block 1310); and indicate, based on the accumulated muscle load data, muscle load status of the exerciser via an exerciser avatar illustrating a plurality of muscles and the muscle load status of each of the plurality of muscles (block 1320).

One example of exercise avatar is shown in FIG. 13B. The exercise avatar may be, for example, 2D or 3D illustration of a human being. For example, the avatar may be stored e.g. on the server 114 and/or the database(s) 112, 290 and displayed on an electronic apparatus such as the PED 106, wrist device 102, or the computing device 200. As shown in FIG. 13B, status of muscles may be indicated (see arrows 1352-1362). The indication may be color based, for example.

Figure 14A:
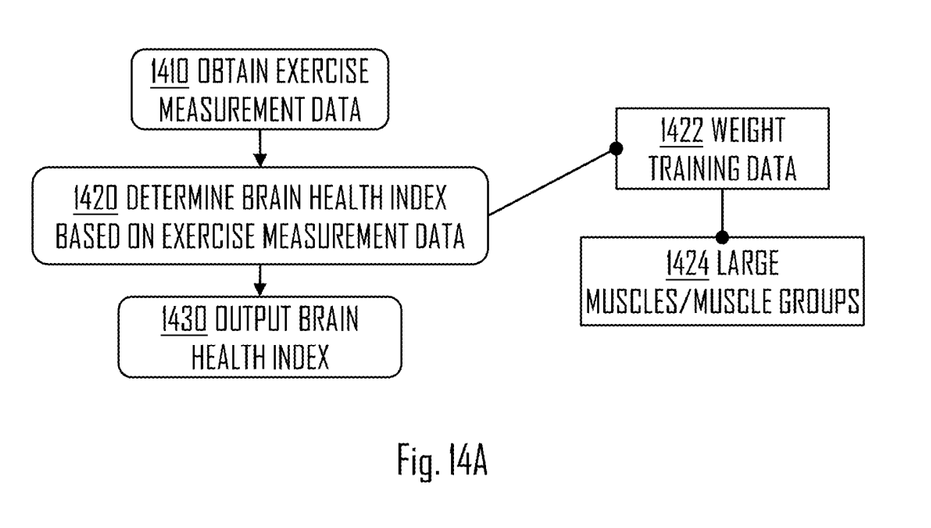

FIG. 14A illustrates an embodiment. Referring to FIG. 14A, the computing device 200 may obtain exercise measurement data (block 1410); determine brain health index based on exercise measurement data (block 1420); and output brain health index (block 1430). The outputted brain health index may be illustrated, for example, in the avatar of FIG. 13B (see reference sign 1390). For example, the brain health index may be indicated with a certain color where the color is associated with certain brain health index. For example, green may indicate good, red may indicate bad and/or yellow may indicate neutral brain health index. Similar color coding can be used for muscles too, for example.

The exercise measurement data, based on which the brain health index is determined, may comprise weight training data 1422 and/or may be based on stress measurements (e.g. HRV). So, the brain health index (or Brain Health Index (BHI)) may depend on how much the user has exercised and particularly how much the user has performed weighted training. Furthermore, the weight training data 1422 may comprise data on large muscles or muscles groups 1424 of the user. For example, larger muscles may refer to glutes, quadriceps, back, chest and/or hamstrings. Therefore, the BHI may be determined, for example, based on measurement data on the large muscles of the user.

In an embodiment, the BHI is determined based on measurement data on leg muscles, such as quadriceps, hamstrings and/or calves. Therefore, leg training may be directly associated with BHI.

Figure 14B:
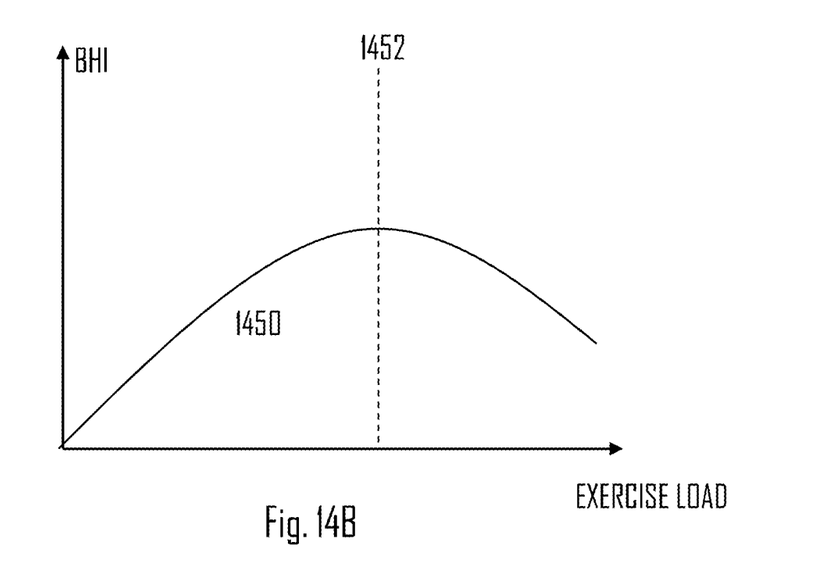

It is noted that BHI may be calculated with one or more correlations between the BHI and performed exercise. In one example, the more the user trains or exercises, the better the BHI gets. However, it is possible that if the user trains too much (e.g. muscle load exceeds a threshold and/or an overall training intensity/load exceeds a threshold), the BHI starts to decrease. One example is shown in FIG. 14B in which correlation between exercise load and BHI is shown. In this example, exercise load may refer to, for example, muscle load of the leg muscles or generally to muscle load of larger muscles. As indicated in FIG. 14B with curve 1450, the BHI may increase as exercise load increases. However, if threshold 1452 (i.e. certain exercise load) is exceed and/or reached, the BHI may start to decrease. It can be understood that if the user trains too much, stress level of the user may increase and recovery from the exercise may take a longer time. This may have a negative effect also on the BHI.

It may be beneficial to indicate the BHI to the user as it may enable (s)he to better plan her/his exercises as a whole. For example, even if muscle load status would indicate that the user should train a certain muscle or muscle group, it may be beneficial to take a day of based on BHI. For example, BHI may exceed the threshold 1452, and thus rest may be recommended. For example, the computing device 200 may take BHI into account when providing training instructions to the user (see e.g. block 1230).

The physical exercise as used above may be understood as a specific movement or movement combination, such as strength training, or sports, such as running, skiing and the like. However, physical exercise may also refer to everyday activities measured during the day. Therefore, the muscle load monitoring system (e.g. FIG. 2) may be used to monitor muscle load of the user throughout the day (e.g. 24/7), and not just when the user is specifically training. Hence, in an embodiment, the system of FIG. 2 is configured to measure muscle load of the user continuously (e.g. 24 hours each day). For this purpose, the conversion framework 220 may comprise entries for various everyday activities, such as walking, movement is stairs (i.e. up or down), vacuuming, standing, to name a few examples. Therefore, in some embodiments, the physical exercise can be understood as physical activity performed by the user.

In an embodiment, physical exercise refers to a specific muscle training, such as strength training, and/or sports, such as running.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware.

In an embodiment, at least some of the processes described in connection with the drawings may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, antenna, antenna circuitry, and circuitry. In an embodiment, the at least one processor, the memory, and the computer program code form processing means or comprises one or more computer program code portions for carrying out one or more operations according to any one of the embodiments of the drawings or operations thereof.

According to yet another embodiment, the apparatus carrying out the embodiments comprises a circuitry including at least one processor and at least one memory including computer program code. When activated, the circuitry causes the apparatus to perform at least some of the functionalities according to any one of the embodiments of the drawings, or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given drawings, as will be appreciated by one skilled in the art.

Embodiments as described may also be carried out in the form of a computer process defined by a computer program or portions thereof. Embodiments of the methods described in connection with the drawings may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium, for example. Coding of software for carrying out the embodiments as shown and described is well within the scope of a person of ordinary skill in the art. In an embodiment, a computer-readable medium comprises said computer program.

Even though the invention has been described above with reference to an example according to the accompanying drawings, the invention is not restricted thereto but can be modified in several ways within the scope of the appended claims. Therefore, all words and expressions should be interpreted broadly, and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. A physical exercise monitoring system for monitoring muscle load of an exerciser, the system comprising:
at least one motion sensor configured to measure motion of the exerciser and to generate motion measurement data as a result of said measuring;
a computing device; and
a database storing in an electronic form a conversion framework comprising a plurality of conversion entries, wherein each conversion entry is associated with a certain type physical exercise and indicates a correlation between the certain type of physical exercise and muscle load coefficient of each of a plurality of muscles, wherein the computing device comprises a processing circuitry configured to cause the computing device to perform operations comprising:
obtaining, from the at least one motion sensor, the motion measurement data measured by the at least one motion sensor on the exerciser during a physical exercise;
determining a type of the physical exercise based on a user input or by detecting the type of the physical exercise from the motion measurement data;
determining, based on the motion measurement data, a number of repetitions of a macroscopic movement performed during the physical exercise;
obtaining, from the database based on a conversion entry corresponding to the determined type of the physical exercise, a muscle load coefficient of one or more muscles loaded in the determined type of the physical exercise;
utilizing the muscle load coefficient of the one or more muscles and the number of repetitions in determining muscle load data indicating muscle specific muscle load caused by the physical exercise performed by the exerciser;
determining, based on the muscle load data, a type of exercise or macroscopic movement that should be employed by the exerciser; and
outputting an indication of the type of exercise or macroscopic movement.

2. The system of claim 1, wherein the physical exercise comprises strength training, wherein the processing circuitry is further configured to cause the computing device to perform operations comprising:
obtaining weight data indicating weight, weights and/or resistance used in the strength training; and
utilizing the weight data in determining the muscle load data.

3. The system of claim 1, wherein the processing circuitry is further configured to cause the computing device to perform operations comprising:
determining, based on the motion measurement data, a number of sets and a number of repetitions in each of the number of sets; and
utilizing the number of sets and the number of repetitions in each of the number of sets in determining the muscle load data.

4. The system of claim 1, further comprising at least one sensor configured to measure respiration of the exerciser and to generate respiration data as a result of said measuring, wherein the determining the number of repetitions is based on the respiration data.

5. The system of claim 4, wherein the processing circuitry is further configured to cause the computing device to perform operations comprising:
performing a sensor fusion algorithm to determine the number of repetitions, wherein the sensor fusion algorithm utilizes the motion measurement data and the respiration data.

6. The system of claim 1, wherein the processing circuitry is further configured to cause the computing device to perform operations comprising:
determining, based on the motion measurement data, a physical exercise intensity metric describing overall intensity of the physical exercise; and
utilizing the physical exercise intensity metric in determining the muscle load data by scaling the muscle specific muscle load based on the physical exercise intensity metric.

7. The system of claim 6, wherein the processing circuitry is further configured to cause the computing device to perform operations comprising:
measuring, after the physical exercise, at least one of heart rate, core temperature of the exerciser; and
utilizing at least one of the heart rate, the core temperature in determining the physical exercise intensity metric.

8. The system of claim 1, wherein the processing circuitry is further configured to cause the computing device to perform operations comprising:
obtaining information indicating at least one muscle that needs to be trained;
determining, based on the conversion framework and the obtained information, one or more physical exercises for training the at least one muscle;
outputting instructions for performing the determined one or more physical exercises; and
monitoring progression of the at least one muscle via monitoring muscle load of the at least one muscle.

9. The system of claim 1, further comprising:
a conversion framework interface communicatively coupled with the database and configured to enable insertion of a conversion entry into the conversion framework without a need to update the entire conversion framework, wherein the conversion entry is associated with a user selected type of physical exercise.

10. The system of claim 1, wherein muscle load coefficients associated with the user selected type of physical exercise are configurable by the exerciser.

11. The system of claim 1, further comprising:
one or more electromyography sensor, wherein, for at least one type of physical exercise, muscle load coefficients are obtained and/or updated based on performing one or more electromyography measurements utilizing the one or more electromyography sensor.

12. The system of claim 1, wherein the type of the physical exercise performed by the exerciser is determined based on the motion measurement data and based on a physical exercise plan.

13. The system of claim 1, wherein the processing circuitry is further configured to cause the computing device to perform operations comprising:
obtaining accumulated muscle load data by determining muscle load caused by a plurality of different exercise sessions; and
indicating, based on the accumulated muscle load data, muscle load status of the exerciser via an exerciser avatar illustrating a plurality of muscles and the muscle load status of each of the plurality of muscles.

14. The system of claim 1, wherein the computing device comprises a wrist device comprising at least one sensor configured to obtain measurement data.

* * * * *